US010908152B2

(12) United States Patent
Shevkoplyas et al.

(10) Patent No.: US 10,908,152 B2
(45) Date of Patent: Feb. 2, 2021

(54) PAPER BASED DIAGNOSTIC TEST

(71) Applicant: The Administrators of The Tulane Educational Fund, New Orleans, LA (US)

(72) Inventors: Sergey S. Shevkoplyas, New Orleans, LA (US); Xiaoxi Yang, New Orleans, LA (US); Julie Kanter Washko, New Orleans, LA (US); Nathaniel Zane Piety, Deerfield, IL (US)

(73) Assignee: The Administrators Of The Tulane Educational Fund, New Orleans, LA (US)

( * ) Notice: Subject to any disclaimer, the term of this patent is extended or adjusted under 35 U.S.C. 154(b) by 0 days.

(21) Appl. No.: 15/215,107

(22) Filed: Jul. 20, 2016

(65) Prior Publication Data
US 2017/0023556 A1    Jan. 26, 2017

Related U.S. Application Data

(63) Continuation of application No. 14/357,074, filed as application No. PCT/US2012/064856 on Nov. 13, 2012, now abandoned.

(60) Provisional application No. 61/692,994, filed on Aug. 24, 2012, provisional application No. 61/558,009, filed on Nov. 10, 2011.

(51) Int. Cl.
| *G01N 30/90* | (2006.01) |
| *G01N 33/52* | (2006.01) |
| *G01N 33/80* | (2006.01) |
| *G01N 30/92* | (2006.01) |
| *G01N 33/66* | (2006.01) |
| *G01N 33/86* | (2006.01) |

(52) U.S. Cl.
CPC .......... *G01N 33/523* (2013.01); *G01N 30/90* (2013.01); *G01N 30/92* (2013.01); *G01N 33/526* (2013.01); *G01N 33/66* (2013.01); *G01N 33/80* (2013.01); *G01N 33/86* (2013.01); *G01N 2333/805* (2013.01)

(58) Field of Classification Search
CPC ............. G01N 2333/805; G01N 30/90; G01N 33/523; G01N 33/526; G01N 33/80
USPC ............ 422/73, 422, 427, 513; 436/10, 177; 210/645
See application file for complete search history.

(56) References Cited

U.S. PATENT DOCUMENTS

| 2009/0298191 | A1* | 12/2009 | Whitesides | .......... G01N 33/523 436/164 |
| 2011/0123398 | A1* | 5/2011 | Carrilho | ................ B01L 3/5023 422/68.1 |
| 2012/0181184 | A1* | 7/2012 | Whitesides | ............. B01L 3/502 205/775 |
| 2013/0034869 | A1* | 2/2013 | Whitesides | ....... B01L 3/502738 435/7.92 |
| 2017/0199177 | A1* | 7/2017 | Kim | ..................... G01N 33/526 |

OTHER PUBLICATIONS

Yang et al. "Integrated separation of blood plasma from whole blood for microfluidicpaper-based analytical devices" Lab Chip, 2012, 12, 274-280 (Year: 2011).*

* cited by examiner

*Primary Examiner* — Dean Kwak
(74) *Attorney, Agent, or Firm* — Burns & Levinson LLP; Richard B. Emmons

(57) ABSTRACT

The present invention relates to simple, low-cost, rapid paper-based diagnostic devices and their methods of use.

21 Claims, 7 Drawing Sheets

PAPER BASED DIAGNOSTIC TEST

COPENDING APPLICATIONS

This application claims priority benefit of U.S. Provisional Application No. 61/692,994 filed Aug. 24, 2012; U.S. Provisional Application No. 61/558,009 filed Nov. 10, 2011; PCT Application No. PCT/US2012/064856 filed Nov. 11, 2012; and U.S. Non-Provisional application Ser. No. 14/357,074 filed May 8, 2014 and all of said applications are incorporated herein by reference as if set forth in full below.

BACKGROUND OF THE INVENTION

I. Field of the Invention

The present invention relates to simple, low-cost, rapid paper-based diagnostic devices and their methods of use.

II. General Background

The analysis of biological fluids is useful for diagnosing a disease or condition and for monitoring the health of individuals and populations. Most current diagnostic assays typically require large and expensive laboratory instruments that must be operated by trained personnel, and further require considerable volumes of biological samples. Thus, most current diagnostic assays can be difficult to implement in remote regions, and are therefore inaccessible for developing countries. Additionally, most current diagnostic assays are not useful for emergency situations or home health care situations. Thus, there remains a need for low-cost diagnostic assays that are not cumbersome and that can be performed on small biological sample volumes.

Microfluidic paper-based devices ("µPADs") are typically small, portable and easily fabricated from inexpensive materials and delivered to remote, resource-limited locations. For example, µPADs may be easily fabricated by printing patterns onto paper with a solid ink (wax) printer and melting the ink to create hydrophobic barriers spanning through the entire thickness of the paper substrate. The µPADs use the paper as a fluidic substrate, and utilize the wicking/capillary properties of the paper to transport the biological sample from a sample deposit region. These devices do not typically require complex laboratory equipment, and thus are well-suited for diagnostic applications in clinical practice generally, and particularly in developing countries, in emergency situations and home health care situations.

Many of these µPADs run colorimetric assays. The use of colorimetric assays for analysis of biological fluids is generally attractive because these assays produce a visual readout and are usually simple to perform, stable, and inexpensive. In colorimetric assays, the biological sample reacts with reagents deposited within a test readout zone, and the reaction produces a detectable color. However, traditional colorimetric assays are limited to optically transparent samples (e.g., water, urine, pre-separated blood plasma). If a non-transparent sample is used, then the color of the sample can interfere with the detection of the developed color.

Blood plasma is commonly used as the biological sample because its composition is exceptionally informative about the pathological processes affecting organs and tissues throughout the body. For example, the detection of non-esterified fatty acids, glucose, heparin and lysophosphatic acid are performed by testing blood plasma. However, in order to use blood plasma in the colorimetric assays, it is beneficial for the plasma to be first separated from the whole blood. Blood plasma separation is a particularly important step for a colorimetric assay because the intense color of the red blood cells ("RBCs") in the whole blood may interfere with quantification of the results of the diagnostic colorimetric assays. Conventional methods for separating blood plasma from the whole blood based on centrifugation or magnetic separation are effective, but require an additional sample preparation step (outside of the diagnostic assay) to isolate plasma from whole blood samples. Plasma purification methods based on the fluid dynamics and rheological behavior of whole blood at the microscale require specifically designed microfluidic devices with fine features to achieve separation; and, thus, are not suitable for use in most clinical situations (and are particularly unsuited for use in the field or home health care situations). Thus, there is a need for innovation in µPADs to allow for integration of the plasma separation step as part of the diagnostic assay. Including the plasma separation step into the design of colorimetric µPADs would transform them into fully integrated diagnostic devices and thus significantly increase their versatility by eliminating the need for a separate sample preparation step which often requires expensive, bulky equipment and specially trained personnel. These fully integrated µPADs would be able to analyze samples of whole blood taken directly in the field and simply placed on the agglutination zone of the device. Integrated plasma separation could make colorimetric µPADs suitable for many more applications and situations in which one may use colorimetric methods to test the multitude of clinically relevant biomolecules present in human blood plasma, while controlling for the interference from the deep-red color presented by the RBCs. Thus, there is a need for an innovation in µPADs in order to allow for point-of-case diagnostics with the ability for automated quantification.

µPADs may also be used to detect the presence of sickling hemoglobin in a blood sample (e.g., to diagnose sickle cell disease). Hemoglobin (Hb) is the iron-containing oxygen-transport protein in RBCs. Each molecule of hemoglobin consists of four globin chains: fetal hemoglobin (Hb F) has two $\alpha$ and two $\gamma$ chains, and adult hemoglobin (Hb A) has two $\alpha$ and two $\beta$ chains. Mutations of the genes controlling the globin chain production include structural variants that change the amino acid sequence and produce aberrant forms of Hb, and mutations that lower or eliminate production of globin chains (thalassaemias). Unlike most other normal and aberrant forms of Hb, deoxy-Hb S changes conformation such that the hydrophobic patch at the site of the valine replacement on a $\beta$ chain of one Hb S molecule binds to a complementary hydrophobic site on a $\beta$ chain of another Hb S molecule. The polymerization of Hb S in an anaerobic environment gives RBCs a distorted, sickled shape.

Those who inherit only one copy of Hb S and possess the other copy of the gene encoding for the normal Hb A (genotype Hb AS) carry the sickle cell trait (SCT), but are generally considered healthy, although with a higher risk for venous thromboembolism and renal medullary carcinoma. Those who inherit two copies of Hb S (genotype Hb SS) develop sickle cell anemia, the most prevalent form of sickle cell disease (SCD). Rarer forms of SCD occur when mutations responsible for other aberrant types of Hb (C or E) or for $\beta$-thalassemias combine with Hb S as a compound heterozygous mutation (genotypes Hb SC, Hb SE, Hb S$\beta$+ or Hb S$\beta^0$). Persons with Hb SS and Hb S$\beta^0$ have the most severe forms of SCD.

An estimated 5% of the world population carries a clinically significant Hb variant. Nearly 85% of SCD incidents and over 70% of all affected births occur in Africa, where even conservative estimates of SCD prevalence suggest a 10.68/1000 rate at birth (compared to 0.49/1000 in the United States). In the United States, approximately 2,000 infants are diagnosed with SCD annually through newborn screening, which is now a national requirement. Although SCD causes significant lifetime morbidity and premature mortality, most affected persons born in high-income countries such as the United States are able to survive into adulthood. In sharp contrast, most affected individuals born in low income countries die before the age of 5 years due to lack of early intervention.

Newborn screening has been the single greatest advance in the treatment of SCD in high-income countries. In the clinical setting, SCD is diagnosed primarily through hemoglobin electrophoresis (HE), but also using high performance liquid chromatography (HPLC) and isoelectric focusing (IEF) testing, which exploit the differences in the electric charge of Hb variants to detect their presence in RBCs of the patient. Performing these diagnostic tests, however, requires a clinical laboratory equipped with specialized instruments, consumable materials and highly-trained technicians, which is expensive and largely unavailable in resource-limited settings of low-income countries where SCD is most prevalent. Thus, in most countries in Africa, universal newborn screening remains prohibitively expensive, and most of the affected individuals are not diagnosed at birth or during their lifetime. The urgent need to develop a low-cost diagnostic test for SCD has been recently recognized as a priority by the World Health Organization.

In addition, the diagnostic tests currently used for SCD in the high-income countries (e.g. HE, HPLC and IEF) require the transfer of blood samples from the point of care to a centralized hospital laboratory, which makes definitive diagnosis of SCD using these tests nearly impossible in the emergency room setting. Therefore, there is a significant need for a rapid test capable of diagnosing SCD at the point of care to confirm the diagnosis in adult patients with unknown medical history seeking emergency treatment for SCD related complications.

The insolubility of deoxy-Hb S in high concentrated phosphate buffers has been widely used by blood banks and clinical laboratories as a simple qualitative method to visually confirm the presence of Hb S in the blood sample. Although the standard Hb solubility test is a low-cost and rapid assay, it cannot distinguish between SCT and SCD because both types of blood samples contain Hb S. Previous modifications of the Hb solubility assay addressing this limitation require extra sample preparation steps, use additional laboratory equipment (e.g. centrifuge, membrane filters) and rely on analytical instruments (e.g. spectrophotometer) to differentiate between SCT and SCD, which makes the test significantly more expensive, complex, time consuming and largely impractical for either the resource-limited or emergency care settings. Thus, there is a need for an innovation in µPADs in order to allow for point-of-case diagnostics with the ability to quickly and simply diagnose SCD.

As will be seen more fully below, the µPADs are substantially different in structure, use and approach from that of other µPADs, and address the problems known in the field, such as those discussed above.

While certain novel features of this invention shown and described below are pointed out in the claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention.

SUMMARY OF THE PRESENT INVENTION

An aspect of the present invention includes a diagnostic device comprising a substrate having pores, an agglutination zone, and a test readout zone, wherein said agglutination zone is functionalized with an agglutinating agent.

A further aspect of the present invention includes a method of diagnosing a disease or condition comprising the steps of providing a diagnostic device comprising a substrate having pores, an agglutination zone, a test readout zone, and wherein said agglutination zone is functionalized with an agglutinating agent and said test readout zone is functionalized with an assay reagent; depositing a blood sample onto said agglutination zone; allowing said blood sample to develop; and observing said test readout zone.

A still further aspect of the present invention includes a method of diagnosing a disease or condition comprising the steps of providing a diagnostic device comprising a substrate having pores and an agglutination zone; mixing a volume of blood sample with a volume of agglutinating agent; depositing a droplet of said mixture onto said agglutination zone; allowing said droplet to develop and create a blood stain pattern on said substrate; and observing said blood stain pattern.

A still further aspect of the present invention includes a method of diagnosing a disease or condition comprising the steps of: providing a diagnostic device comprising a substrate having pores, wherein said substrate further comprises an agglutination zone and a test readout zone, and wherein said agglutination zone is functionalized with an agglutinating agent and said test readout zone is functionalized with an assay reagent; depositing a blood sample onto said agglutination zone; allowing said blood sample to develop; and observing said test readout zone.

A still further aspect of the present invention includes a method of diagnosing a disease or condition comprising the steps of: providing a diagnostic device comprising a substrate having pores, wherein said substrate further comprises an agglutination zone; mixing a volume of blood sample with a volume of agglutinating agent; depositing said droplet onto said agglutination zone; allowing said droplet to develop and create a blood stain pattern on said substrate; and observing said blood stain pattern.

A still further aspect of the present invention includes a system for diagnosing a disease or condition comprising: a substrate having pores, wherein said substrate further comprises: an agglutination zone and a test readout zone; wherein said agglutination zone is functionalized with an agglutinating agent; an optical image capture device capable of capturing an image of said test readout zone; and computer software capable of analyzing said image.

A still further aspect of the present invention includes a system for diagnosing a disease or condition comprising: a substrate having pores, wherein said substrate further comprises an agglutination zone; and a sample deposited on said agglutination zone, wherein said sample is comprised of a mixture of whole blood and an agglutinating agent; an optical image capture device capable of capturing an image of said substrate; and computer software capable of analyzing said image.

A still further aspect of the present invention includes a device for diagnosing a disease or condition comprising: a means for receiving a blood sample; a means for agglutinating red blood cells of said blood sample; a means for transporting plasma of said blood sample away from said receiving means; and a means for determining the presence of an analyte in said plasma.

A still further aspect of the present invention includes a device for diagnosing a disease or condition comprising: a means for receiving a sample comprised of: whole blood mixed with a means for agglutinating said whole blood; a means for transporting soluble forms of Hb of said sample away from said receiving means and creating a blood stain pattern; a means for scanning said blood stain pattern; and a means for correlating said scanned blood stain pattern with said diagnosis of said disease or condition.

The above and other objects and features of the present invention will become apparent from the drawings, the description given herein, and the appended claims.

BRIEF DESCRIPTION OF THE DRAWING

For a further understanding of the nature and objects of the present invention, reference should be had to the following description taken in conjunction with the accompanying drawings in which like parts are given like reference numerals.

DETAILED DESCRIPTION OF THE PREFERRED EMBODIMENT

One aspect of the present invention provides a diagnostic device and its method of use for separating blood plasma from red blood cells (RBCs) in small samples of whole blood contained entirely within a µPAD.

Separation of Plasma from RBCs Using RBC Agglutination

Figure 1A:
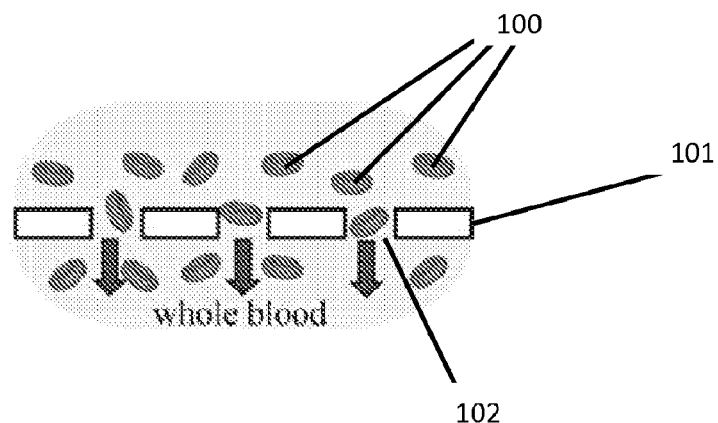
FIG. 1A illustrates the known RBC characteristic of deformability when RBCs are attempted to be separated from whole blood.
Figure 1B:
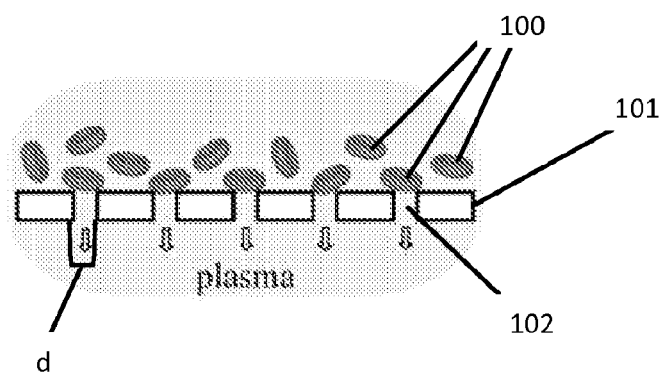
FIG. 1B illustrates the known method of filtering plasma from RBCs in whole blood.

As depicted in FIG. 1A, normal healthy RBCs 100 are extremely deformable, and can easily pass through a substrate 101 with pores 102 smaller than the diameter of the RBCs 100. The substrate 100 may be paper, specifically chromatography paper, cloth, string or any other material with wicking or capillary properties. The diameter of the smallest pore 102 that that a RBC 100 could pass through depends on the volume and surface area of the cell, but is approximately 2.5 µm for a normal human RBC. Therefore, a substrate 101 with pores 102, each with a diameter (d) of less than 2.5 µm, provides a fairly straightforward means for separating plasma from RBCs 100 in the whole blood samples, as illustrated in FIG. 1B. However, because the rate of flow (Q) through a pore 102 scales with the fourth power of the pore 102 diameter (d), $Q \propto d^4$, the smaller the diameter (d) of the pores 102 of the substrate 101, the less the volumetric flow rate of plasma through the substrate 101. Additionally, filtered RBCs tend to pack very efficiently above the substrate 101 (because of their deformability), which ultimately leads to complete secession of flow of plasma through the substrate 101. Thus, although substrates 101 with pores 102 smaller than 2.5 µm could separate plasma from RBCs 100 very effectively, the yield of purified plasma may not be sufficient for colorimetric assays. Conversely, increasing the diameter of the pores 102 would increase the flow of purified plasma through the substrate 101, but would inevitably reduce the efficiency of separation.

Figure 1C:
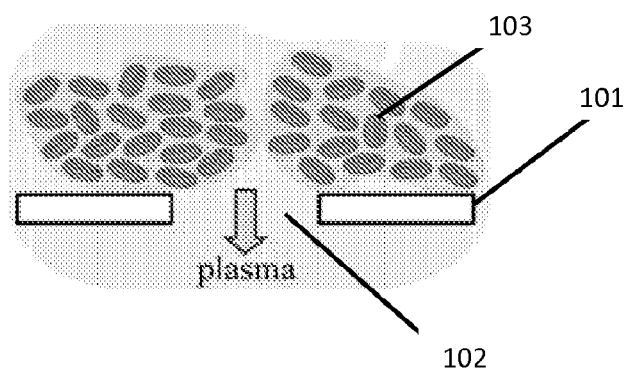
FIG. 1C illustrates the use of RBC agglutination to filter plasma from RBCs in whole blood.

As illustrated in FIG. 1C, the present invention utilizes RBC agglutination to increase the effective size of RBCs by forming large multi-cellular agglutinated RBCs 103 that can be filtered out using a substrate 101 with pores 102 significantly larger than 2.5 µm, and thus produce purified plasma at a much higher volumetric flow rate. Agglutination, generally, is the clumping of particles, such as RBCs, to create a larger particle. Agglutination can be caused by the addition of an agglutinating agent, or alternatively by a change in temperature. Because of agglutination, RBCs form agglutinated RBCs 103 that are too large to pass through the pores 102 within the substrate 101 of the µPAD. As a result, agglutinated RBCs 103 become entangled in the substrate 101 and thus separate from the plasma in a whole blood sample. The plasma, which passes through the pores 102 of the substrate 101, is then wicked outwardly through the substrate 101. In the present invention, the pores 102 in the substrate 101 are sufficiently small to efficiently filter out the agglutinated RBCs 103, yet large enough to enable adequately high rates of blood plasma flow for completing a colorimetric assay.

Agglutination can be initiated by adding an agglutinating agent, such as agglutinating antibodies (anti-A,B) to whole blood. Anti-A,B are monoclonal antibodies of the immunoglobulin class IgM, which selectively bind to antigen A and antigen B present on the surface of human RBCs. Direct agglutination of RBCs by anti-A,B antibodies occurs when either A or B, or both A and B antigens are present on the surface of RBCs (blood types A, B and AB).

Figure 2A:
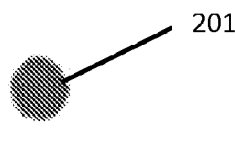
FIG. 2A illustrates the result of spotting whole blood on untreated paper.
Figure 2B:
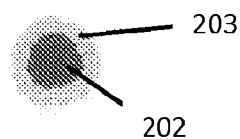
FIG. 2B illustrates the result of spotting whole blood on paper treated with agglutinating antibodies anti-A,B.

FIG. 2A depicts the visual appearance of a whole blood sample spotted onto paper substrate treated with phosphate buffered saline (for control) and FIG. 2B depicts the visual appearance of a whole blood sample spotted onto paper treated with agglutinating antibodies. Comparing FIG. 2A to FIG. 2B, one can see that the whole blood sample 201 spotted on paper pre-treated with phosphate buffered saline (for control) behaved as a uniform phase with RBCs and plasma wicking through the paper without separation. However, when a whole blood sample was deposited on paper pre-treated with a solution of anti-A,B antibodies, the plasma separated from agglutinated RBCs 202 (that became entangled in the paper fibers), creating a plasma band 203 around the agglutinated RBCs 202. The plasma band 203 spread significantly further than agglutinated RBCs 202 or the whole blood sample 201 on phosphate buffered saline treated paper.

Figure 2C:
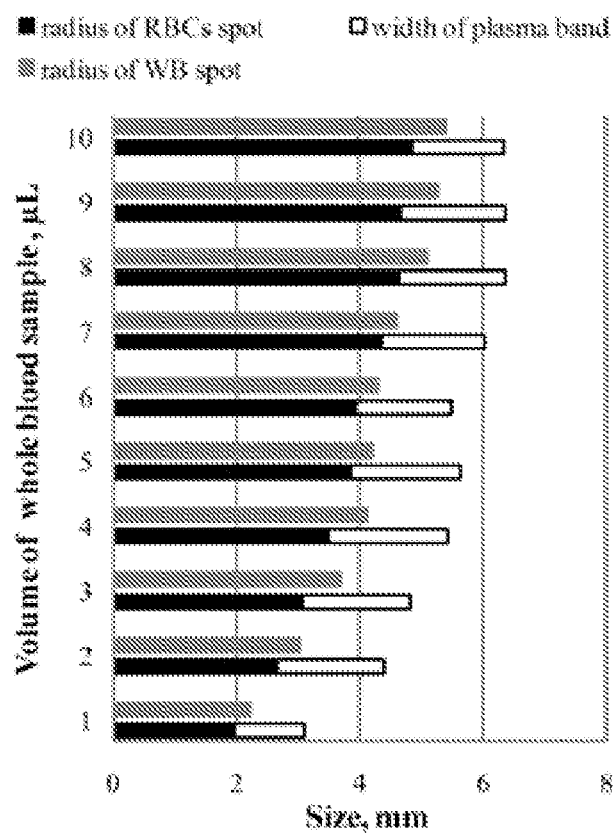
FIG. 2C illustrates the relation between volume of the whole blood sample and the radius of the whole blood spot, radius of the agglutinated RBC spot and the width of the plasma band.

By spotting 15 μL of either the anti-A,B solution or phosphate buffered saline (for control) onto chromatography paper, allowing the paper to dry, adding samples of whole blood with volumes ranging from 1 μL to 10 μL, and then measuring the radius of the spot created by the whole blood sample treated with phosphate buffered saline (control) and the radius of the RBC spot and the width of the plasma band created by the whole blood sample on paper treated with agglutinating antibodies, we found that the width of the band created by the separated plasma did not depend significantly on the volume of the whole blood sample deposited on paper treated with anti-A,B antibodies. This can further be seen in FIG. 2C which illustrates the radius of the whole blood spot, radius of the agglutinated RBC spot and the width of the plasma band in millimeters for various volumes of whole blood samples.

μPAD Device Utilizing RBC Agglutination

Figure 3:
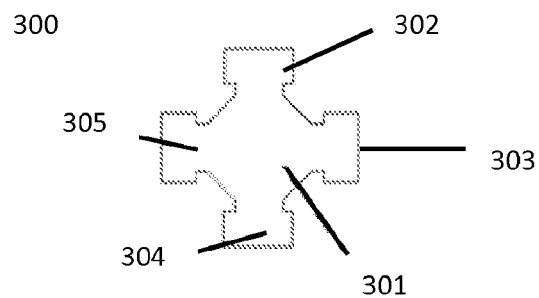
FIG. 3 illustrates the design of a µPAD with integrated blood plasma separation.

FIG. 3 illustrates the design of a μPAD 300 integrating blood plasma separation from whole blood using agglutination. The pattern of the μPAD 300 includes the agglutination zone 301 in the center region and four test readout zones 302, 303, 304, 305 on the periphery of the μPAD 300. The aforementioned data (illustrated in FIG. 2C) was used to determine the optimal shape and size of the μPAD 300 for effectively retaining agglutinated RBCs within the central part of the μPAD 300 and enabling the flow of a sufficient amount of separated plasma into the test readout zones 302, 303, 304, 305 on the periphery. The optimal distance between the center of the agglutination zone 301 to the outer edge of the test readout zones 302, 303, 304, 205 is approximately 0.5 cm.

The μPAD 300 was optimized to operate on approximately 7 μL whole blood samples, which corresponds to the amount of blood one could easily obtain with a finger prick and to the volume of blood sample required for many rapid diagnostic tests currently available in resource-limited settings.

The test readout zones 302, 303, 304, 305 of the μPAD 300 were made in a rectangular shape to simplify analysis of the color change in the test readout zones 302, 303, 304, 305. The rectangular shape of the test readout zones 302, 303, 304, 305 of the μPAD 300 design enables their automated selection when color change quantification is done by scanning and computer analysis. However, the test readout zones may be of any shape.

The μPADs 300 may be fabricated by printing the pattern of many μPADs 300 (for example, arranged in an array) onto chromatography paper (for example, Whatman No. 1 chromatography paper, Piscataway, N.J.) using a solid-ink (wax) printer (for example, a Phaser 8560N, Xerox, Norwalk, Conn.) and then heating the patterned paper on a hot plate at 150° C. for 3 minutes, and allowing said paper to cool to room temperature to enable the formation of hydrophobic barriers through the full thickness of the paper. The melting process results in widening of the printed line, which was accounted for when originally designing the pattern of the μPAD. The μPAD 300 is then functionalized by spotting (i) a solution of anti-A,B antibodies onto the agglutination zone 301, preferably of a volume in the range of 1-20 μL, (ii) reagents of the colorimetric assay 301, preferably of a volume in the range of 1-20 μL, onto each of the three of the test readout zones 302, 303, 304, and (iii) phosphate buffered saline 301, preferably of a volume in the range of 1-20 μL, onto one remaining test readout zone 305. The test readout zone 305 treated with phosphate buffered saline is used for color change calibration. Each functionalized μPAD 300 is then allowed to dry before further use.

Use of μPAD Utilizing RBC Agglutination

Figure 4A:
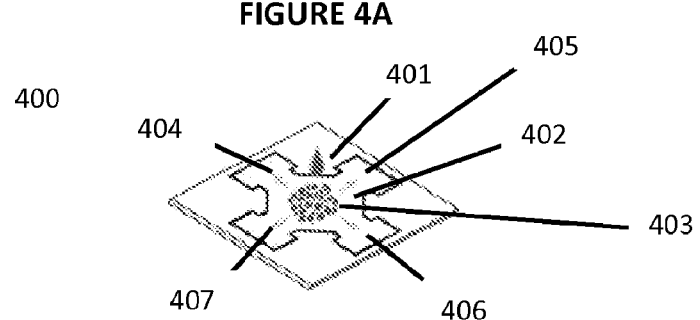
FIG. 4A illustrates the operation of a µPAD with integrated blood plasma separation.
Figure 4B:
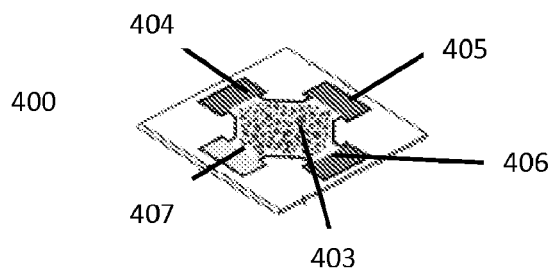
FIG. 4B illustrates a µPAD with integrated blood plasma separation after the reaction at the test zones has occurred.

Referring now to FIGS. 4A and 4B, to perform a colorimetric assay of a whole blood sample using the μPAD 400, 7 μL drop of whole blood sample 401 is deposited onto the agglutination zone 402 in the center of the μPAD 400. The whole blood sample 401 spreads to fill the agglutination zone 402, which acts as a 'catch basin' for the whole blood sample 401 and retains agglutinated RBCs 403 while allowing the plasma to wick laterally outwards into the test readout zones 404, 405, 406, 407 on the periphery of the μPAD 400. The separated plasma fills the test readout zones 404, 405, 406, 407 where the analyte of interest of the plasma reacts with the reagents of the colorimetric assay producing a color change proportional to the concentration of the analyte of interest of the plasma. In FIG. 4B, test readout zones 404, 405, 406 are functionalized with the reagent of the colorimetric assay, thus resulting in a color change in those readout zones 404, 405, 406, and test readout zone 407 is not functionalized with the reagent of the colorimetric assay (and may instead be functionalized with phosphate buffered saline), thus acting as a control, and not resulting in a color change. Generally, it takes less than 5 minutes from the introduction of the whole blood sample 401 for RBC agglutination 403, blood plasma separation and detectable color change in the test readout zones 404, 405, 406 to occur.

EXAMPLE 1

Determination of Plasma Glucose Concentration in Whole Blood Samples

A μPAD with RBC agglutination-based plasma separation was tested using an assay for plasma glucose as an example. In this assay, glucose oxidase catalyzes oxidation of glucose present in the sample of plasma to yield hydrogen peroxide ($H_2O_2$). Horseradish peroxidase then catalyzes the reaction of $H_2O_2$ with potassium iodide, which results in brown color. The intensity of the color change is proportional to the amount of $H_2O_2$ produced, and thus to the amount of glucose.

Figure 5:
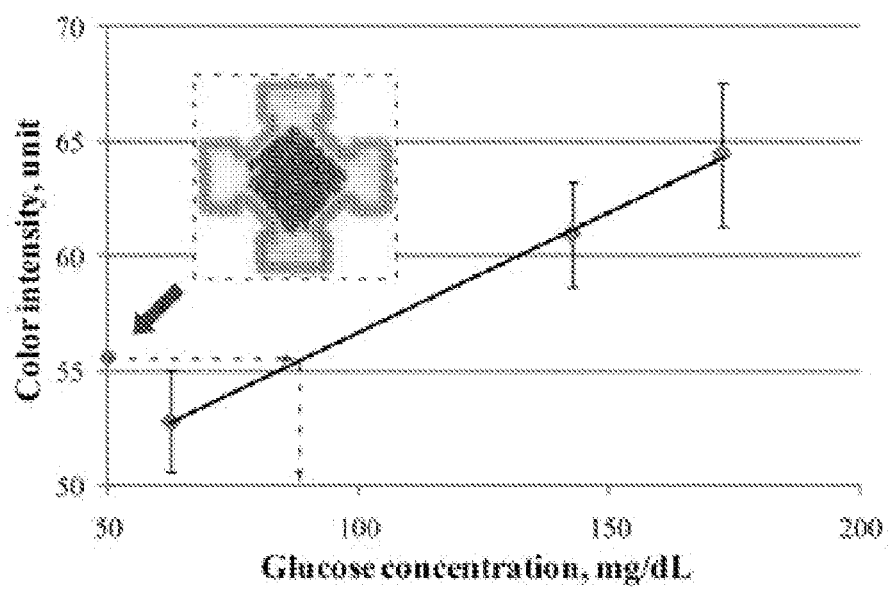
FIG. 5 illustrates the quantification of glucose concentration in whole blood samples using a µPAD with integrated blood plasma separation.

To calibrate the sensitivity of the colorimetric assay to plasma glucose, 3.5 μL of plasma with different known concentrations of glucose was spotted onto square-patterned regions of chromatography paper (the same paper used to fabricate the μPADs and with observed pores of approximately 2-200 μm in diameter) that were pre-treated with the reagents of the assay. The plasma was prepared by centrifugation (800×g, 15 minutes) of whole blood samples (taken from human venous blood collected from healthy consenting volunteers). Plasma concentration was measured spectrophotometrically (500 nm, NanoDrop 1000, Nano Drop products, Wilmington, Del.) following the manufacturer's instructions for Liquid Glucose (Oxidase) Reagent Set (Pointe Scientific, Inc.). Some of the square-patterned regions were treated with 1 μL of phosphate buffered saline to use as the color change control. The assays were allowed to develop for 5 minutes, the paper scanned, images imported into MATLAB®, and the color change for the various concentrations of glucose quantified. FIG. 5 shows the calibration curve for the dependence of the color change on the concentration of glucose in plasma within the physiological range (50-200 mg/dL).

In fabricating a µPAD 400 capable of performing this colorimetric assay for plasma glucose directly on a whole blood sample 401, the same colorimetric assay was functionalized in the three test readout zones 404, 405, 406 of the µPAD 400 to perform the measurement on the same sample 401 in triplicate, although in principle different colorimetric assays for the same analyte or colorimetric assays for different analytes could be used. The three test readout zones 404, 405, 406 were each functionalized with 1 µL of a solution consisting of potassium iodide (0.6M in deionized water), starch (0.3 g/mL in saturated salt solution), glucose oxidase (100 U/mL in 0.1M potassium phosphate, pH 7.4, 0.05 M NaCl, 5 mM cholic acid, 0.1% Triton® X-100), and horseradish peroxidase (20 U/mL in 0.1M potassium phosphate, pH 7.4, 0.05 M NaCl, 5 mM cholic acid, 0.1% Triton® X-100). The fourth test readout zone 407 was treated with 1 µL of phosphate buffered saline to control for changes in brightness and background color. The agglutination zone 402 was functionalized with 7 µL of Seraclone Anti-A,B (ABO3) clones BS 63/BS 85 (Biotest Medical Diagnostics GmbH, Germany). All reagents were allowed to dry before use of the µPAD 400.

To test a whole blood sample 401 (taken from human venous blood collected from healthy consenting volunteers with A, B or AB blood types) with an unknown concentration of glucose using the µPAD 400, 7 µL of the sample 401 was deposited onto the agglutination zone 402 of the µPAD and allowed to develop for 5 minutes. Next, the color change in the test readout zones 404, 405, 406 of the µPAD 400 was quantified by scanning the chromatography paper containing the µPAD 400 on a portable scanner (for example, a CanoScan LiDE110, Canon USA Inc, Lake Success, N.Y.), and analyzing the images in MATLAB® (The MathWorks Inc, Natick, Mass.). Finally the color change value was converted into the plasma glucose concentration using the calibration curve for the assay (as shown in FIG. 5). However, a smart phone equipped with a digital camera could also be used to complete this part of the assay. The concentration of glucose in the whole blood sample was 89.5 mg/dL when measured with the µPAD 400, and 82.5 mg/dL when measured independently using a conventional spectrophotometer (NanoDrop 1000).

This experiment used anti-A,B antibodies to induce RBC agglutination in whole blood samples obtained from volunteers with blood type A, B or AB. However, this specific implementation of the separation strategy would not work for those with blood type O (approximately 44% of human population overall) as the blood of those individuals do not contain antigen A or antigen B. Antigen H is present on the surface of all RBCs, including those with blood type O except those of Oh "Bombay phenotype" (less than 0.0004% of human population). Antigen H is the precursor of antigen A and antigen B, and depending on the person's ABO blood type, it is converted into either antigen A or antigen B, or both. Consequently, RBCs of type A, B or AB have significantly less of antigen H than RBCs of type O, and we speculate that anti-H IgM antibodies would induce strong agglutination of type O RBCs and weak agglutination of type A, B or AB RBCs. Thus, we further speculate that the use of IgM antibodies reactive to antigens A, B and H (either as a mixture of anti-H and anti-A,B or a single anti-ABH antibody) will extend the applicability of this plasma separation approach to almost all humans.

While the above experiment used a colorimetric assay to test for glucose concentration, we speculate that other analytes may be tested using their relevant reagents. Examples may include the Sigma triglycerides diagnostic kit to test for non-esterified fatty acids; diphenylcarbazide containing diphenylcarbazone to test for free fatty acids; amplex Red, cholesterol oxidase, horseradish peroxidasein phosphate buffered saline for cholesterol; azure A assay for heparin; and lysophospholipase, peroxidase, G3PO, G3PDH, HSD, NADH, cholic acid, TOOS and 4-aminoantipyrine to HEPES buffer (pH 7.6) containing 0.01% Triton X-100 for lysophosphatidic acid.

Another aspect of the present invention provides a diagnostic device and method for separating Hb A, C and F from deoxy-Hb S in small samples of whole blood contained entirely within a µPAD in order to detect the presence of sickling hemoglobin in a blood sample.

Separation of Hb A, C and F from Hb S Using Agglutination

Known in the prior art are regular Hb solubility assays, such as SickleDex (SickleDex™, Streck, Omaha, Nebr.), that use saponin to chemically lyse RBCs in the blood sample, releasing Hb into solution where, in the presence of sodium hydrosulfite (an inexpensive and safe reducing agent), the freed Hb is converted to deoxy-Hb. In a highly concentrated phosphate buffer, deoxy-Hb S changes conformation, polymerizes and precipitates, visibly clouding the solution (the solubility of non-sickling forms of Hb remains unaffected). Because of the polymerization, Hb S molecules agglutinate to form large supra-molecular agglomerates, which significantly increases their effective size with respect to the other types of Hb.

Conventional, commercially available Hb solubility assays (such as the SickleDex) are useful for differentiating normal (Hb AA) blood samples from those containing Hb S, but they are incapable of distinguishing between SCT (Hb AS) blood and blood from SCD patients (Hb SS, Sβ or SC) because all of these samples contain some Hb S. Thus, there is a need for an innovation in µPADs to allow for the separation of Hb A, C and F from the whole blood as part of the diagnostic assay.

One aspect of the present invention is a µPAD addressing the aforementioned problem by using agglutination to separate Hb S from Hb A, C and F. A drop of whole blood mixed with the components of a Hb solubility assay deposited onto a substrate will result in polymerized deoxy-Hb S (resulting from the release of Hb into solution where, in the presence of sodium hydrosulfite, the freed Hb is converted to deoxy-Hb and polymerizes). The substrate may be paper, specifically chromatography paper, cloth, string or any other material with wicking or capillary properties. The polymerized deoxy-Hb S of the whole blood will then remain in the center of the blood stain, unable to pass through the pores of the substrate and entangled by the substrate, while molecules of Hb A, C and F remain soluble and are transported laterally to the periphery of the stain by capillary action. Normal, SCT and SCD samples can then be easily differentiated based on the characteristic blood stain patterns produced by each sample.

Figure 6:
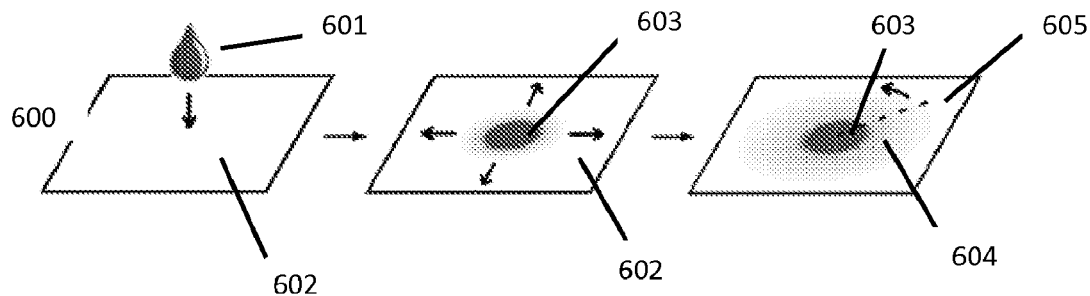
FIG. 6 illustrates a schematic diagram of the use of a paper-based hemoglobin solubility assay utilizing agglutination.

FIG. 6 illustrates the operating principle of the paper-based Hb solubility assay schematically. To perform the paper-based Hb solubility assay, a drop of blood, between 10-50 µL in volume, is added to an agglutinating agent, in this instance, SickleDex solution. The SickleDex solution is added so that the volume ratio for the blood sample to SickleDex solution is 1:20. A droplet of this mixture 601 is deposited onto the paper substrate 602 of the μPAD 600. The agglutinates of polymerized deoxy-Hb S, as well as the cellular debris, cannot pass through the pores of the paper substrate 602, are entangled by the paper substrate 602 and remain within the outline of the original droplet, creating a red spot 603 in the center of the developing blood stain. Soluble forms of Hb present in the droplet are transported laterally outwards, creating a pink ring 604 around the center red spot 603. The overall diameter of the blood stain and the diameter of its center red spot 603 are determined by the volume of the droplet 601 deposited onto the paper substrate 602, and are independent of the type of the sample. The color intensity of the pink ring 604, however, strongly correlates with the concentration of soluble forms of Hb (e.g. Hb A, F or C) present in the blood sample.

μPAD Utilizing Hb S Agglutination

Figure 7A:
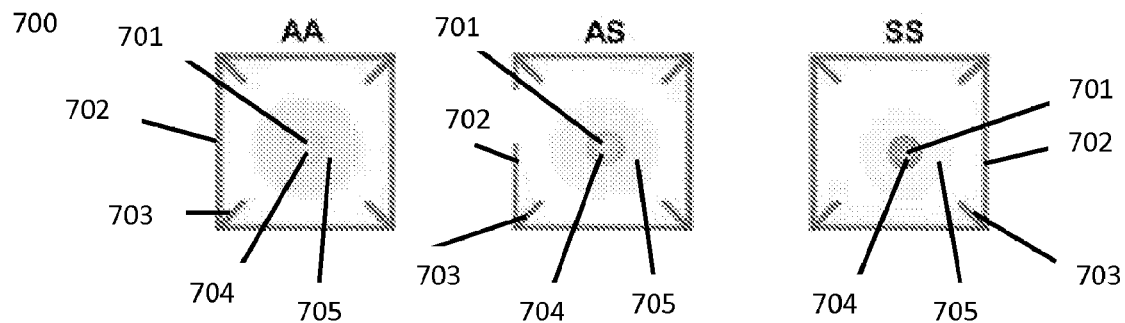
FIG. 7A illustrates the blood stain patterns created during the use of a paper-based hemoglobin solubility assay utilizing agglutination.

FIG. 7A illustrates the design of a μPAD utilizing agglutination to separate Hb S from whole blood. The μPAD 700 includes square shaped hydrophobic barriers 702 and an agglutination zone 701 in the center region. The square pattern of the hydrophobic barriers 702 of the μPAD 700 was designed to limit the spread of blood from one μPAD 700 to another, thus preventing the potential cross-contamination of samples. The 45° alignment lines 703 in each corner of the μPAD 700 provided the operator with visual guides for depositing the sample droplets in the agglutination zone 701 in the center of the μPAD 700. The simplistic design of the μPAD 700 also significantly simplifies automated image analysis used to digitize and analyze the blood stain pattern. However, it is not necessary to use a specially shaped μPAD 700—a simple piece of chromatography paper would be sufficient to perform the assay. The pattern of the hydrophobic barriers 702 were drawn in black lines on white background using illustration software (for example, Canvas 11, ACD Systems International Inc., Seattle, Wash.), and then printed on sheets of chromatography paper (for example, No. 1, Whatman, Piscataway, N.J.) using a solid-ink printer (for example, a Phaser 8560N, Xerox, Norwalk, Conn.). The printed chromatography paper was heated on a hot plate (150° C., 3 minutes) above the melting point of the wax to enable the formation of hydrophobic barriers 702 through the full thickness of the paper. The melting process resulted in widening of the printed line, which was accounted for when originally designing the pattern of the μPAD 700.

Use of μPAD Utilizing Hb S Agglutination

Referring again to FIG. 6, to perform a paper-based Hb solubility assay of a whole blood sample using the μPAD 600, a small volume, approximately 10-50 μL of whole blood, is gently mixed with the SickleDex solution at a 1:20 ratio by volume, 5 minutes allowed to elapse, and then a 20 μL droplet of the mixture is deposited onto the center of the μPAD 600. The droplet spreads radially from the center through the paper substrate 602, forming a characteristic blood stain pattern. The resulting blood stain is then digitized with a portable scanner and analyzed.

The blood stain pattern analyzed using an image processing algorithm. The quantification of the blood stain is significantly simplified by the natural symmetry of the blood stain. The computer algorithm automatically detects the geometric center of the stain, and the image is rotated with a 1° step about the center to collect 360 independent one-pixel-wide horizontal line scans of the blood stain (one such line scan is illustrated by the dashed line 605). These line scans are then averaged to obtain a single curve representative of the pattern of the red color intensity change from the center of the blood stain to its periphery. Examples of such curves for blood samples containing Hb AA, Hb AS and Hb SS are shown in FIG. 7B.

Figure 7B:
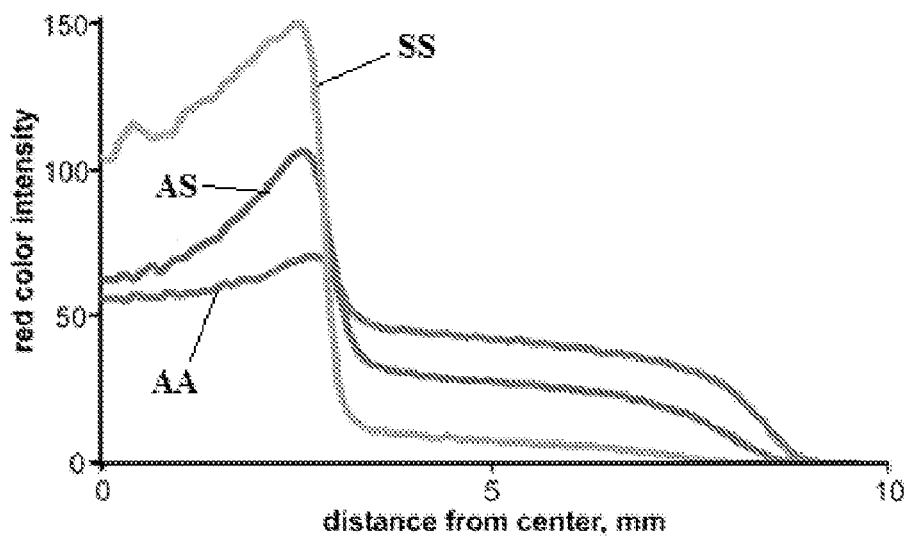
FIG. 7B illustrates red color intensity profiles quantifying the blood stain patterns shown in FIG. 7A.

As can be seen in FIG. 7B, the red color intensity curves have approximately the same overall profile for all types of blood samples. The color intensity increases gradually from the center of the stain, reaching maximum at the interface of the center spot and the peripheral pink ring. This characteristic change in color across the center spot is speculated to be due to the transport of polymerized Hb S agglomerates with the radial outflow of liquid towards the contour left by the deposition of the original droplet. The color of the pink ring is relatively uniform, fading into the background at the outer edge of the stain. The uniformity in color of the pink ring is speculated to be due to the fact that the color of the pink ring is determined by the concentration of the soluble forms of Hb, which remain uniformly dissolved at the molecular level in the high-phosphate buffer solution.

EXAMPLE 2

Classification of Blood Samples as Healthy, SCT or SCD

The μPAD of the present invention was used on one normal (Hb AA), one SCT (Hb AS) and one SCD (Hb SS) blood sample as representative examples. We gently mixed a small volume, approximately 10-50 μL, of each sample of whole blood with the SickleDex solution at a 1:20 ratio by volume, waited 5 minutes and deposited a 20 μL droplet of each of the mixtures onto the center of a μPAD. Normal human venous blood (Hb AA)) was collected from healthy consenting volunteers; SCD (Hb SS) and SCT (Hb AS) blood samples were obtained at the Sickle Cell Center of Southern Louisiana (New Orleans, La.). Blood samples from SCD patients who received blood transfusion in the previous three months were excluded. The Hb A, F, C and S content of SCD samples was determined via hemoglobin electrophoresis as a part of standard patient care. SCT blood samples were collected from biological parents (usually mothers) of SCD patients. SCT samples with hematocrit values lower than 25% (indicating anemia) were excluded. The SickleDex solution (SickleDex™, Streck, Omaha, Nebr.) used in this experiment is a commercially available test kit that consists of two components: (i) saponin and sodium hydrosulfite supplied as dry reagent power, and (ii) 2.3M potassium phosphate solubility buffer with 0.1% 2-chloroacetamide. The contents of one vial containing the reagent powder were added to one bottle of the solubility buffer (as provided by the manufacturer) and dissolved completely with vigorous agitation. The solution of the Hb solubility assay was mixed with blood at 1:20 ratio by volume.

The droplet deposited on each μPAD spread radially from the center through the paper substrate, forming a characteristic blood stain pattern for each of the three types of samples, as depicted in FIG. 7A. The size of the μPAD and the volume of the droplet were such that the outermost margin of the stain could not reach the alignment lines and pattern outline on the periphery of the μPAD. The sheets of chromatography paper containing arrays of μPADs with blood stains were inserted into a portable flatbed scanner (CanoScan LiDE110, Canon USA Inc., Lake Success, N.Y.). However, a smart phone equipped with a digital camera could also be used to complete this part of the assay. The scanned images were analyzed with an image algorithm (MATLAB®, The MathWorks Inc., Natick, Mass.) and digitized to produce the red color intensity profiles shown in FIG. 7B. It took about 10 minutes to complete all operations of the assay, including the introduction of the sample onto the µPAD, the formation of the blood stain, scanning of the images and finally the automated image analysis. In contrast, a standard Hb electrophoresis test normally used to diagnose SCD takes at least 2 hours and often as long as about a week.

Referring still to FIG. 7A, although each of the three blood samples produced a stain of similar size, with a darker red spot 704 (~3 mm radius) in the center of the µPAD (outlining the original placement of the sample droplet), and a lighter pink ring 705 (~5.5 mm width) on the periphery of the µPAD, we observed a visually striking difference between the blood stain patterns. The color of the blood stain produced by normal blood (Hb AA) was almost uniform throughout, with a slightly darker contour outlining the center spot 704 (due to what we speculate to be the deposition of the cellular debris produced by the lysis of RBCs). The center spot 704 of the blood stain produced by SCT blood (Hb AS) was significantly darker and the pink ring 705 on the periphery was significantly lighter than that of the normal sample. The center spot 704 of the blood stain produced by SCD blood (Hb SS) was the darkest of the three samples, and the pink ring 705 on the periphery of the µPAD was barely visible.

Because Hb S (which polymerizes when deoxygenated in a concentrated phosphate buffer) is responsible for the color of the center spot, and other forms of Hb (which remain soluble under the same conditions) are responsible for the color of the pink ring, these differences can be explained by the significant disparity in the fraction of Hb S and the soluble forms of Hb present in RBCs of each sample. Generally, the Hb S content of RBCs from healthy subjects (Hb AA) is 0%, for SCT subjects (Hb AS) the Hb S content varies around 20-40%, and for SCD subjects (Hb SS) it can be as high as 80-100%. Thus, the SCD (Hb SS) sample, which had the highest fraction of Hb S and the lowest fraction of soluble Hb (e.g. Hb A, F or C), produced the darkest center spot and a practically invisible pink ring on the periphery.

Figure 8A:
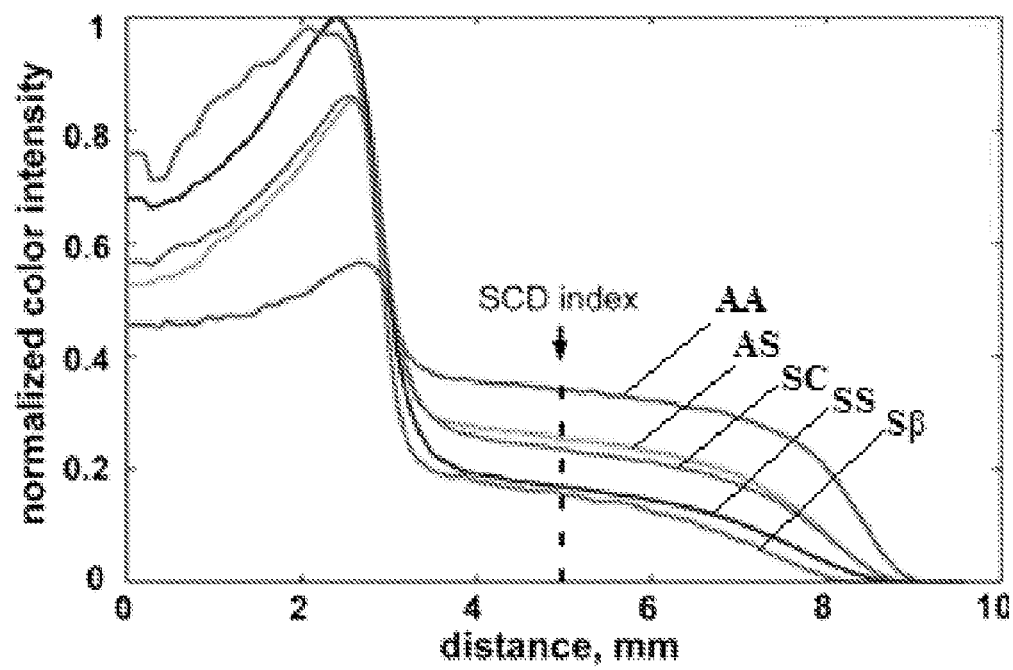
FIG. 8A illustrates color intensity profiles of normal (Hb AA), SCT (Hb AS) and SCD (Hb SS, Hb Sβ or Hb SC) blood samples.
Figure 8B:
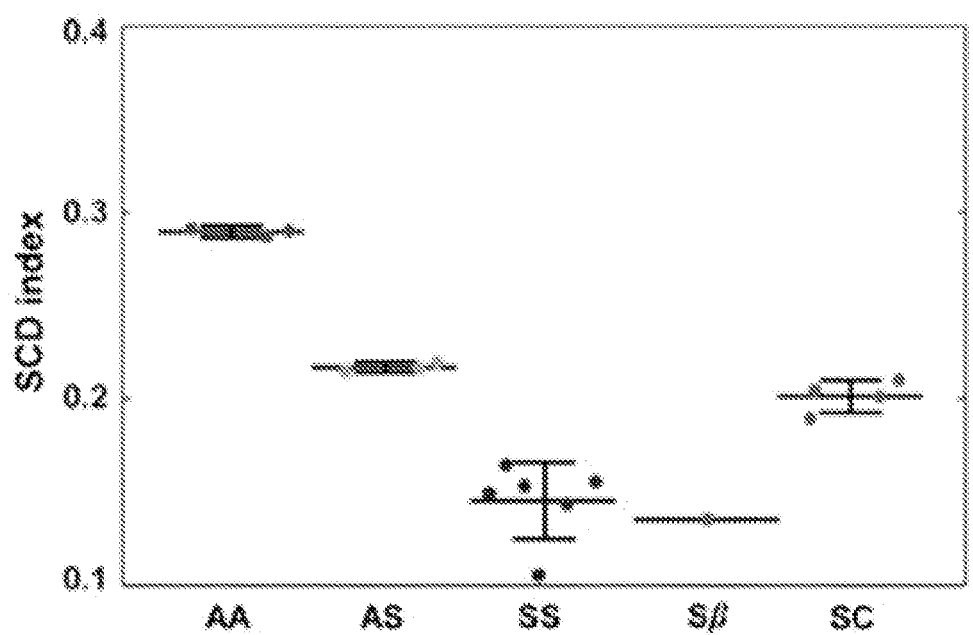
FIG. 8B illustrates normalized color intensity values at 5 mm for each sample of FIG. 8A.

Thus the differences between the blood stain patterns can be used to distinguish between blood samples from healthy, SCT and SCD subjects. FIG. 8A shows the normalized color intensity profiles of blood stains for samples from normal (Hb AA), SCT (Hb AS) and SCD (Hb SS, Hb Sβ, Hb SC) subjects. The color intensity profiles were normalized by the total area under the curve (which reflects the Hb concentration in the original sample) to account for the differences in hematocrit among subjects, and then averaged over all subjects within each Hb genotype. The normalized color intensity at a distance of 5 mm from the center of the blood stain (dubbed SCD index and shown by the dashed line in FIG. 8A) was highly consistent between the subjects from the same Hb genotype group, and showed the most obvious difference between the groups. The physical meaning of the SCD index is the fraction of Hb in the sample that remains soluble when deoxygenated in concentrated phosphate buffer. As shown in FIG. 8B, we used the SCD index as a quantitative metric to differentiate samples among Hb genotypes. The dots represent individual blood samples for each blood genotype (Hb AA (3), Hb AS (3), Hb SS (6), Hb Sβ (1), and Hb SC (4)) and the SCD index value for that individual sample. The three horizontal lines of each blood genotypes Hb AA, Hb AS, Hb SS and Hb SC) correspond to the mean of the samples (the center horizontal line) and one standard deviation above and below the mean (the top and bottom horizontal lines, respectively). Our experiment only included one sample for blood genotype Hb Sβ, and as such, that sample includes only a mean and no standard deviation could be calculated. Thus, from FIG. 8B, it can be observed that the majority of the samples analyzed using this method resulted in SCT values within one deviation from the mean. From FIG. 8B, one can also see that the SCD index for normal (Hb AA) samples was significantly higher ($p<0.001$) than for any other type of samples tested (either SCT or SCD). The SCD index for blood samples from SCT (Hb AS) individuals was significantly higher ($p<0.001$) than for patients with Hb SS and Hb Sβ$^0$ (the two most common and severe forms of SCD), and distinctively (although less significantly) higher ($p<0.05$) than that for patients with Hb SC (a less common, milder form of SCD). The difference between Hb SS/Sβ group and Hb SC was also highly significant ($p<0.001$), positioning the patients with Hb SC between generally healthy SCT individuals and patients with more severe forms of SCD in terms of the SCD index. Because of the significant differences in SCD index values among the Hb genotypes, this SCT index value proves effective for identifying a blood sample as being normal (Hb AA), SCT (Hb AS) and SCD (Hb SS, Hb Sβ, Hb SC).

Furthermore, we speculate that the µPAD of the instant invention may be used to diagnose the following diseases and infections using the following corresponding agglutinating agents: Acquired myasthenia gravis and Acetylcholine Receptor Antibody; Mycoplasma pneumoniae and cold agglutinins; Infectious mononucleosis and cold agglutinins; Influenza and cold agglutinins; Nonbacterial infection and cold agglutinins; Collagen vascular diseases and cold agglutinins; Cirrhosis and cold agglutinins; Leukemia, lymphoma, and multiple myeloma and cold agglutinins; Salmonella and febrile agglutinins; Rickettsia and febrile agglutinins; Brucellosis and febrile agglutinins; Tularemia and febrile agglutinins; Leukemia and febrile agglutinins; Lymphoma and febrile agglutinins; Human immunodeficiency virus and HIV antibody; Human immunodeficiency virus and urine HIV antibody; Human immunodeficiency virus and saliva HIV antibody; Asthma and IgE antibody; Dermatitis and IgE antibody; Food allergy and IgE antibody; Latex allergy and IgE antibody; Allergic rhinitis and IgE antibody; Angioedema and IgE antibody; Systemic lupus erythematosus and anticardiolipin antibody; Antiphospholipid syndrome and anticardiolipin antibody; CREST syndrome and anticentromere antibody; Systemic lupus erythematosus and anti-DNA antibody; Chronic hepatitis and anti-DNA antibody; Infectious mononucleosis and anti-DNA antibody; Biliary cirrhosis and anti-DNA antibody; Goodpasture syndrome and antiglomerular basement membrane antibody; Autoimmune glomerulonephritis and antiglomerular basement membrane antibody; Lupus nephritis and antiglomerular basement membrane antibody; Autoimmune hepatitis and anti-liver/kidney microsomal antibody; Hypergammaglobulinemia and anti-liver/kidney microsomal antibody; Syphilis and antimitochondrial antibody; Rheumatic heart disease and antimyocardial antibody; Streptococcal infection and antimyocardial antibody; Cardiomyopathy and antimyocardial antibody; Pernicious anemia and anti-parietal cell antibody; Juvenile diabetes and anti-parietal cell antibody; Scleroderma and antiscleroderma antibody; Chronic active hepatitis and anti-smooth muscle antibody; Mononucleosis hepatitis and anti-smooth muscle antibody; Viral hepatitis and anti-smooth muscle antibody; Chronic thyroiditis and antithyroglobulin antibody; Rheumatoid arthritis and antithyroglobulin antibody; Thyrotoxicosis and antithyroglobulin antibody; Hypothyroidism and antithyroglobulin antibody; Chronic thyroiditis and antithyroid peroxidase antibody; Rheumatoid arthritis and antithyroid peroxidase antibody; Thyrotoxicosis and antithyroid peroxidase antibody; Hypothyroidism and antithyroid peroxidase antibody; Acute fungal infection and fungal antibodies IgG, IgA and IgM; Celiac disease and gliadin antibodies and endomysial antibodies; Legionnaires disease and legionnaires disease antibody; Erythema infectiosum and parvovirus B19 antibody; Transient aplastic anemia and parvovirus B19 antibody; Chronic anemia and parvovirus B19 antibody; Immune thrombocytopenia and platelet antibody; Rabies and rabies-neutralizing antibody; Rubella infection and rubella antibody; Rubeola infection and rubeola infection; Toxoplasmosis and toxoplasmosis antibody; and West Nile virus and West Nile virus antibody.

The invention claimed is:

1. A diagnostic device comprising:
a substrate having pores and a thickness;
a sample loading zone, wherein the sample loading zone includes a separation zone that separates agglutinates from non-agglutinates in a circumferential direction which extends outwardly from the sample loading zone;
one or more test readout zones; and
a hydrophobic barrier forming a perimeter around the sample loading zone and the one or more test readout zones.

2. The diagnostic device of claim 1, wherein the sample loading zone directly receives a sample comprising whole blood.

3. The diagnostic device of claim 1, wherein the hydrophobic barrier is wax.

4. The diagnostic device of claim 3, wherein the substrate is selected from the group consisting of chromatography paper, cloth, string and any material having wicking or capillary properties.

5. The diagnostic device of claim 4, wherein the substrate is chromatography paper.

6. The diagnostic device of claim 1 wherein said pores of said substrate are in the range of about 2 µm to about 200 µm in diameter.

7. The diagnostic device of claim 1, wherein the hydrophobic barrier is square shaped or cross shaped.

8. The diagnostic device of claim 7, further comprising four alignment lines, wherein one of the four alignment lines is located within each corner of the square shape.

9. The diagnostic device of claim 8, wherein each of the one or more test readout zones is positioned at a circumferential distance from the sample loading zone.

10. The diagnostic device of claim 8, wherein each arm of the cross shape has an equal length.

11. The diagnostic device of claim 10, wherein each of the one or more test readout zones is positioned at an outer end of each arm of the cross shape.

12. The diagnostic device of claim 1, wherein the sample loading zone directly receives a sample which has a volume ranging from 1 µL to 10 µL.

13. The diagnostic device of claim 1, wherein the separation zone includes an agglutinating agent that forms the agglutinates in the substrate.

14. The diagnostic device of claim 13, wherein the agglutinating agent includes agglutinating antibodies or heat.

15. The diagnostic device of claim 1, wherein the separation zone does not include an agglutinating agent that forms the agglutinates in the substrate.

16. The diagnostic device of claim 1, wherein retention of the agglutinates in the sample loading zone indicates that the sample is from a subject having either sickle cell trait (SCT) or sickle cell disease (SCD).

17. The diagnostic device of claim 1, wherein the sample loading zone is positioned centrally relative to the perimeter formed by the hydrophobic barrier.

18. The diagnostic device of claim 17, wherein the one or more test readout zones are positioned between the sample loading zone and the perimeter.

19. The diagnostic device of claim 1, wherein at least one of the one or more test readout zones includes at least one assay reagent for a colorimetric assay.

20. The diagnostic device of claim 1, wherein at least one of the one or more test readout zones includes a control reagent.

21. The diagnostic device of claim 1, wherein the diagnostic device detects sickle cell trait and sickle cell disease.

* * * * *